United States Patent [19]

Hawthorne

[11] 4,037,602
[45] July 26, 1977

[54] ADAPTABLE DIAPER

[76] Inventor: Janet R. Hawthorne, 556 Riford Road, Neenah, Wis. 54956

[21] Appl. No.: 661,449

[22] Filed: Feb. 26, 1976

[51] Int. Cl.² ............................................. A16F 13/16
[52] U.S. Cl. ..................................... 128/287; 128/284
[58] Field of Search ........... 128/287, 284, 286, 290 R, 128/290 H, 288

[56] References Cited

U.S. PATENT DOCUMENTS

| 3,150,663 | 9/1964 | Combs | 128/287 |
|---|---|---|---|
| 3,554,195 | 1/1971 | Murdoch | 128/284 |
| 3,559,648 | 2/1971 | Mason, Jr. | 128/287 |
| 3,794,038 | 2/1974 | Buell | 128/287 |
| 3,881,488 | 5/1975 | DeLanty et al. | 128/287 |
| 3,926,189 | 12/1975 | Taylor | 128/287 |

Primary Examiner—Stephen C. Pellegrino
Attorney, Agent, or Firm—Dominik, Knechtel, Godula & Demeur

[57] ABSTRACT

A diaper assembly having versatile uses and applications for boys and girls, each diaper assembly having a substantially rectangular diaper material and a pair of trapezoidal liners mounted to the inside of the diaper material, the bases of the trapezoidal liners being removably attached at the opposite ends of the diaper material, and the tapered ends overlapping at a central location of the diaper material. One of the diaper liners may be removed, and the diaper with the remaining liner is positioned at the front for the boy user and at the back for a girl user. The removed liner may be overlaid relative to the remaining liner to thicken the liners when placing the diaper on the child for overnight use.

10 Claims, 7 Drawing Figures

U.S. Patent    July 26, 1977    4,037,602
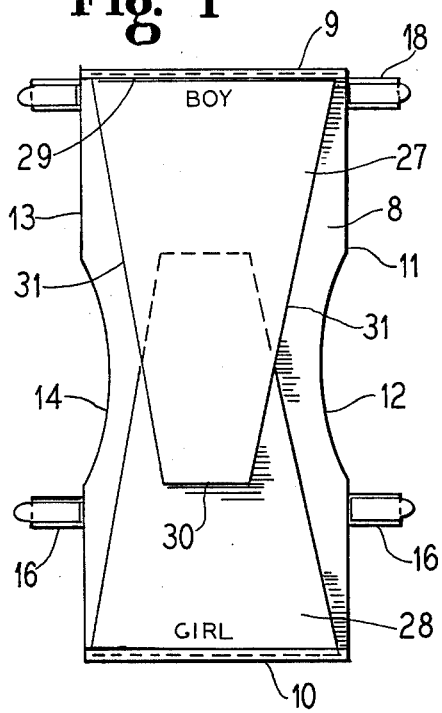
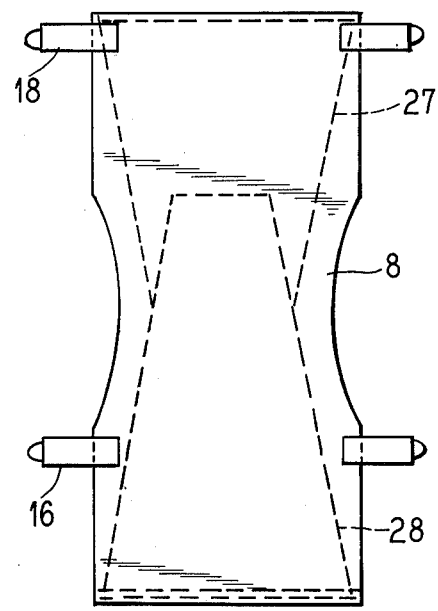
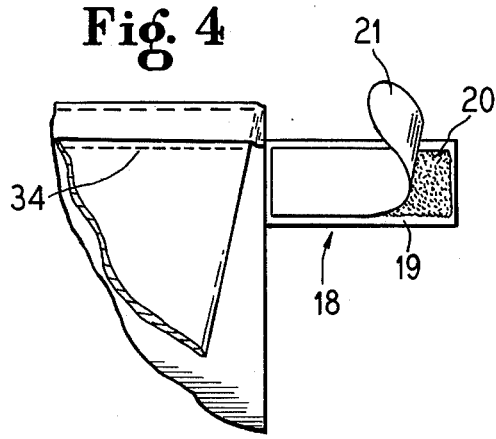
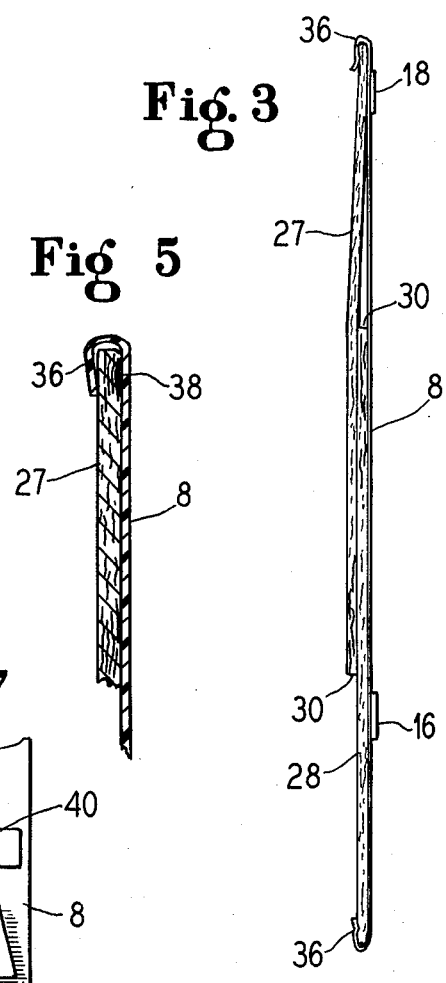
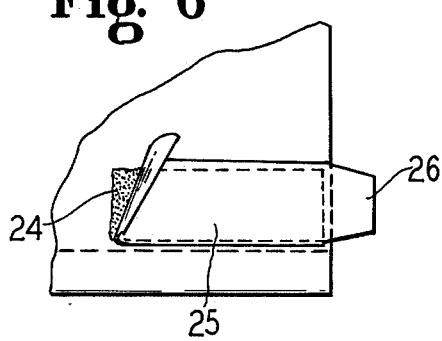
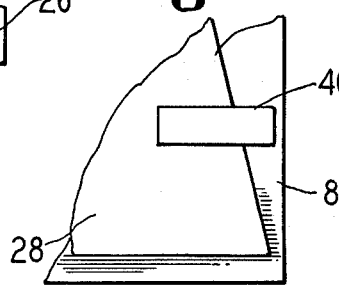

ADAPTABLE DIAPER

This invention relates to a diaper assembly which is provided with a pair of liners on one side, each liner being removably attached to the diaper material; and the invention particularly relates to such diaper assembly wherein one of the liners may be removed so the remaining liner may be selectively positioned on infants and toddlers with preferred orientation for boys and girls.

Disposable diapers have been provided in which the substantially rectangular diaper material has packed cellulosic fibers, and the outside of the diaper material has a plastic sheath, usually adhered to the outside of the diaper material. Such disposable diapers have also been provided with a diaper liner on the inside, which is usually of thicker material such as fluffed batting to absorb urine of the user. Representative disposable diapers are shown, for example in U.S. Pat. No. 3,554,195.

Some attention has been directed in this art to the problem of meeting peculiar requirements of wetting habits between boys and girls. Boy users heavily wet the diaper in the front and girl users heavily wet the diaper in the back. For example, U.S. Pat. No. 3,766,922 teaches a specially designed liner which is attached to a diaper material, the liner being specifically designed either for use with a boy or with a girl. The end of the liner is shown to be thickened when a diaper is selected with such a liner for use with a boy. Another liner is thickened in a more central portion when a diaper with such a liner is selected for a girl.

The art has therefore not directed adequate attention to the specialized problems of diapers for boys or girls, especially disposable diapers. Where attention has been directed to this problem, the solution has been plagued by specialization in the design of the diaper either for a boy or a girl. Otherwise, standard diaper materials with standard absorbent liners must be commonly used for boys or girls, infants or toddlers, without meeting the particular problems associated with such different users.

One object of the present invention is to provide an improved diaper assembly wherein a pair of liners are provided on a single diaper material, with provision for removing one of the liners and selectively mounting the diaper with the remaining liner in front position for a boy or in back position for a girl. It is an advantage of this object that the total liner bulk is reduced by removing one of the liners so that the used is not made uncomfortable with material accumulation, particularly at the junction areas between legs and torso. Yet still another advantage and feature of this object is the advantageous provision of cutouts at the opposite sides of the diaper material so that the resulting scalloped edges further reduce bulk or material accumulation when the diaper assembly is placed on the user.

Yet still another object of the present invention is an improved diaper assembly, of the type described, wherein high degrees of versatility are provided in the use of a diaper assembly, having a pair of liners removably attached to the diaper material. One removed liner can be superimposed over the remaining liner to preferentially increase the absorbent bulk when the diaper assembly is selectively placed in the front for boys, or the liner is in the back for girls. It is a feature and advantage of this object that the liner bulk can be increased for a greater absorption of urine without unduly increasing the bulk of the diaper assembly material between the legs of the user. Such liner build up can be provided when opportunity is lacking for frequent changes of the diaper, or during overnight use.

It is still yet another object of the present invention to provide an improved diaper assembly of the type described wherein a disposable diaper having the recited advantages can be economically manufactured to provide economy to the consumer so that a single diaper assembly can be purchased for both boys and girls, each diaper assembly having a liner which is substantially identical in area and shape.

In addition to economies of manufacture, the consumer can remove either one of the liners, and still use the remaining liner selectively for a boy or for a girl.

These objects attained together with still other objects, which will occur to practitioners from time to time, upon considering the following disclosure of the invention, which includes drawings wherein:

FIG. 1 is a plan view of the inside of the diaper assembly;

FIG. 2 is a plan view of the outside of the diaper assembly;

FIG. 3 is a side elevational view of the diaper assembly, on a slightly enlarged scale;

FIG. 4 is a fragmentary view of a corner of the diaper assembly shown in FIG. 1, but on an enlarged scale;

FIG. 5 is a fragmentary side elevational view of one end of the diaper assembly, and on an enlarged scale;

FIG. 6 is a fragmentary view similar to that of FIG. 4, but illustrating an alternative embodiment of fastening means; and FIG. 7 is a fragmentary plan view showing an alternative embodiment for removably attaching a liner to diaper material.

Looking first at FIGS. 1 and 2, there is shown a conventional diaper material 8 in a general rectangular form. Such diaper material has opposed ends 9, 10. A side 11 joins the ends and such side has a cutout which forms a scalloped edge 12 to accomodate the leg of the user in the usual way. An opposite side 13 also joins the opposite ends, and this side likewise has a cutout forming a scalloped edge 14, for the same purpose. The particularly illustrated diaper assembly is designed for toddlers in that fastening means, shown as leg tabs 16, are attached to the sides at the scalloped edges, and other fastening means, shown as waist tabs 18, are attached to the sides near one of the ends. Such fastening means or waist tabs allow the diaper assembly to be fastened at the waist, while the other fastening means or leg tabs allow the diaper assembly to be fastened at the leg areas. For infants, fastening means or tabs would be provided only near one or both of the ends of the diaper.

Looking now at FIG. 4, the tab is shown in greater detail as including a flexible body 19 having an adhesive film 20 thereon. Such adhesive film is covered by a removable barrier 21, which may be paper or plastic. Removing the barrier 21 exposes the adhesive film so that it may be wrapped around the outside of the diaper material at the other end, after the diaper is folded around the user.

The view of FIG. 6 shows an alternative embodiment wherein the inside of the diaper material has an adhesive film strip 24, protected by a removable barrier 25 having a handle portion 26, which extends beyond the side of the diaper material. Removal of the barrier exposes the adhesive film strip so that such strip can be fastened to either an inside or outside corner of the diaper material at the other end.

Looking again at FIGS. 1 and 2, as well as FIG. 3, there is seen a first tapered liner 27 and an opposed second tapered liner 28 on the inside of the diaper material 8. Each diaper liner is shown as having a trapezoidal configuration, and one liner has a shape and area coincidental with the shape and area of the other liner.

The trapezoidal configuration includes a base 29 which extends substantially to the opposite sides of the diaper material. Opposite the base is a smaller or tapered end 30 which is joined to the base by tapering sides 31. The tapered ends of the liners are in overlapping relationship at a central portion of the diaper material. This assures a sufficient length to each liner, relative to a boy, to extend from an up-front location to a down-location. Likewise, it assures a sufficient length, relative to a girl, to extend from an up-back position to a down bottom position. It is seen that the tapered ends 30 extend only a minor distance of the width between the opposite sides of the diaper material. The down bottom area of the user requires a smaller area for absorbency than either the up front or down back areas.

Each of the liners are removably attached along the base at a respective end of the diaper material. The removable fastening means are shown in FIG. 4 as a linear perforation that extends along the base to the opposite tapering sides of the liner. Other reduced thickness breakpoints may be provided substantially at this point. The base portion of greater width above the linear perforation may be securely attached to the diaper material inside a fold 36 as shown in FIG. 5. Additionally, a continuous bond line or bond points can hold the liner to the diaper material, such as point 38 which is shown. The fold is not required, and the liner may be removably attached to the diaper material by a rupturable bond point similar to 38.

Another alternative means for fastening a liner to the diaper material is indicated in the view of FIG. 7. A tab connector 40 is shown holding the liner 28 to the diaper material 8. This connector tab may be rupturable paper bonded to the liner and to the diaper material, or it can be a removable tab which is held by an adhesive film to the liner and to the diaper material.

Still other means will occur to practitioners for removably attaching the liner to the diaper material.

In use, the first or second liner is removed by releasing the attaching means along the base at an end of the diaper material. The attaching means are located at the base of the liner so that substantially the entire liner may be removed. The remaining liner is positioned at the front of the boy user, the larger end of the liner being at the up-front and the smaller or tapered end being at the down-bottom. For a girl, the liner is positioned at the back so the larger area is at the up-back and the smaller or tapered end is at the down-bottom.

The absorptive capacity is increased by superimposing the removed liner over the remaining liner when the liners are disposed in coincidental relationship. Removed liners can be reserved for such occasions when the absorptive liner bulk is to be increased, as preparing a child for overnight sleeping or when opportunity does not allow more frequent changes.

Removing one of the liners understandably reduces bulk when the diaper is mounted to the user, and this reduced bulk will reslt in greater comfort to the infant in the crib or the toddler when walking or crawling. The scalloped edges 12, 14 contribute to this greater comfort since they reduce the bulk around the leg area in the usual way. Even where the second liner is superimposed over the first liner, the bulk problem is not aggravated since the liners are located either at the front or back of a particular boy or girl user. While these diapers, particularly in disposable form, find special advantage in use with infants and toddlers, they may also be used for incontinent adults. Its use as training pants for children will also be appreciated.

The claims of the invention are now presented and the terms of such claims may be further understod by reference to the preceding specification and the views of the drawings.

What is claimed is:

1. A diaper assembly selectively adaptable for use with a boy or a girl, including
   a planar diaper material having opposite sides and ends, an inside end and outside end,
   a first tapered absorbent liner on the inside of the diaper material. said first tapered absorbent liner having a base, an oppositely smaller end and tapering sides connecting the base and smaller end, said liner base being attached by releasable attaching means to a diaper material end, and the smaller end extending beyond the mid-point between the opposite diaper material ends, and
   a second tapered absorbent liner having a base, an oppositely smaller end and tapering sides, the liner base of said second liner being attached at the other of the diaper material ends by a second releasable attaching means, said tapered end of the second tapered absorbent liner extending beyond the mid-point between the opposite diaper material ends and being in overlapping relationship with the smaller end of the first tapered absorbent liner,
   whereby one of said liners may be removed at its base by releasing the attaching means so that the remaining liner may be selectively positioned relative to a boy or a girl, and the removed liner may be layered with the remaining liner to thicken the selected liner position.

2. A diaper assembly which includes the features of claim 1 wherein the bases of said first and second absorbent liners extend substantially to the opposite sides of the diaper material, and said smaller end is a minor portion of the distance between the sides of the diaper material.

3. A diaper assembly which includes the features of claim 2 wherein said base is removably attached by linear perforations extending to the tapering sides.

4. A diaper assembly which includes the features of claim 3 wherein said base is removably attached by a rupturable bond point.

5. A diaper assembly which includes the features of claim 3 wherein said base is removably attached by a releasable connector between the liner and the diaper material.

6. A diaper assembly which includes the features of claim 5 wherein said releasable connector is a tab removably adhered to the tapered liner and to the diaper material.

7. A diaper assembly which includes the features of claim 1 wherein each side of the diaper material has a scalloped edge to accommodate the legs of the user when the diaper is placed in use.

8. A diaper assembly which includes the features of claim 7 wherein said diaper material has mounted tab fastener means adjacent each of the opposite diaper material ends so said ends may be attached at the waist of infants.

9. A diaper assembly which includes the features of claim 8 wherein said diaper material further includes fastener means mounted at each of the scalloped edges so that the diaper may be mounted along the legs and the waist of a toddler.

10. A diaper assembly which includes the features of claim 1 wherein each of the absorbent liners have a generally trapezoidal configuration, each liner having an area coincidental with the other, and said diaper material and liners being formed of disposable cellulosic materials.

* * * * *